United States Patent [19]

Burton

[11] Patent Number: 4,721,508

[45] Date of Patent: Jan. 26, 1988

[54] OSTOMY PROSTHESIS

[75] Inventor: Thomas A. Burton, Rochester, Minn.

[73] Assignee: Waters Instruments, Inc., Rochester, Minn.

[21] Appl. No.: 658,766

[22] Filed: Oct. 9, 1984

[51] Int. Cl.[4] .............................................. A61F 5/445
[52] U.S. Cl. ..................................... 604/338; 604/98; 604/277
[58] Field of Search .................. 604/96, 277, 332, 333, 604/334, 335, 338, 339, 342, 337, 98

[56] References Cited

U.S. PATENT DOCUMENTS

| | | | |
|---|---|---|---|
| 2,504,872 | 4/1950 | Perry | 604/334 |
| 2,584,540 | 2/1952 | Botvin | 604/342 |
| 3,520,301 | 7/1970 | Fenton | 604/338 |
| 3,802,418 | 4/1974 | Clayton | 604/96 X |
| 4,381,765 | 5/1983 | Burton | 604/338 X |

Primary Examiner—Harland S. Skogquist
Attorney, Agent, or Firm—James R. Haller

[57] ABSTRACT

An ostomy prosthesis comprising a drainage tube securable at one end within an ostomy stoma deep to the fascia, and a skin-contacting plate to which the other tube end is secured. The prosthesis includes an ostomy bag having a mouth securable to the plate about the stoma. Closure means, operable from outside the bag, is provided to open and close the passageway defined by the drainage tube and plate to control the flow of bowel contents into the bag.

9 Claims, 7 Drawing Figures

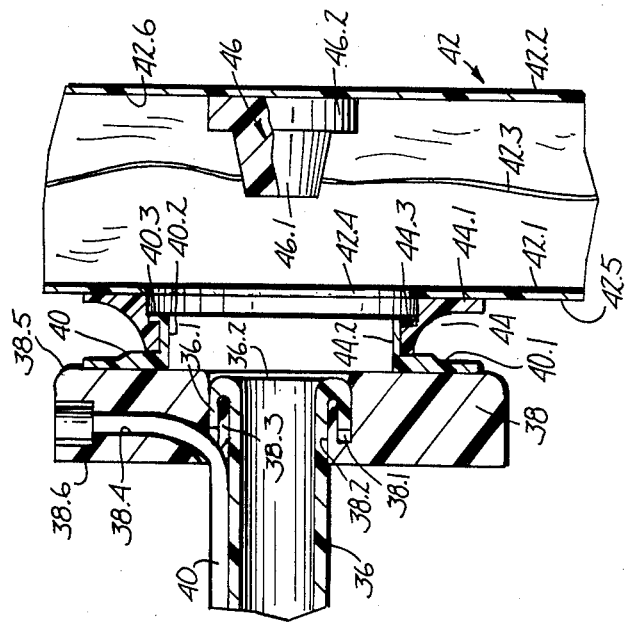
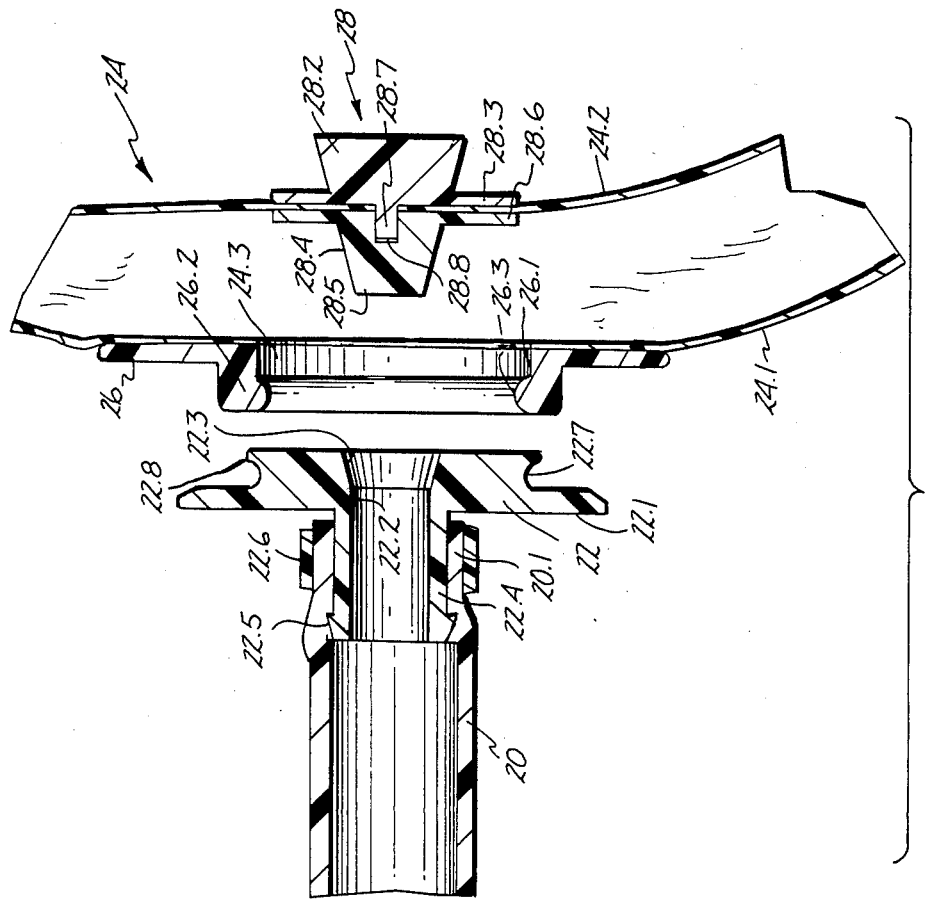

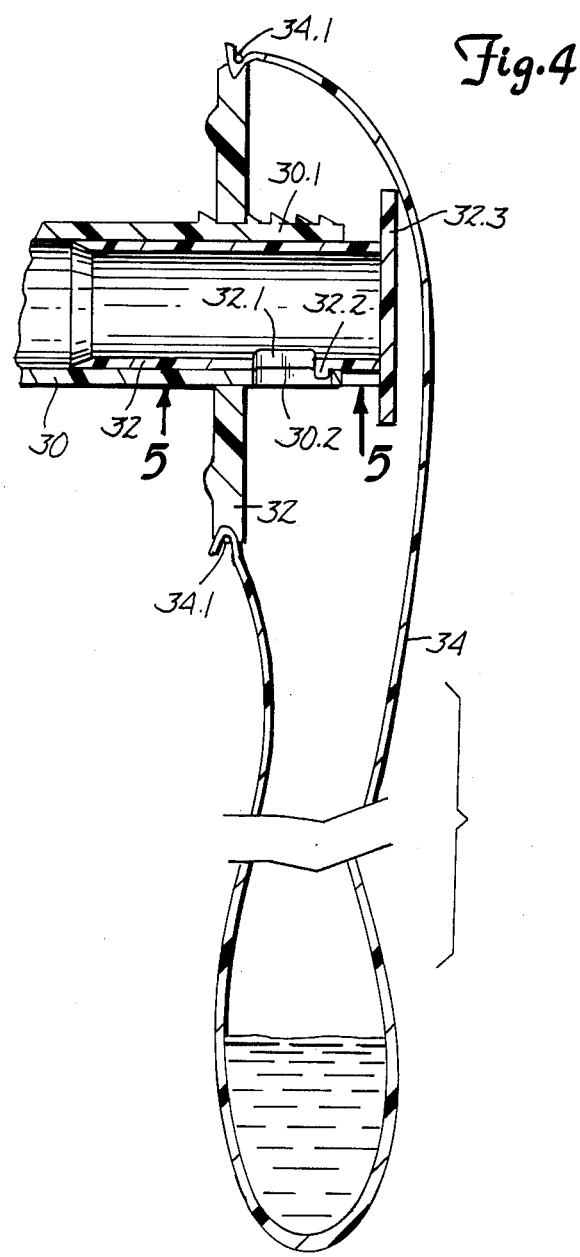
Fig.4
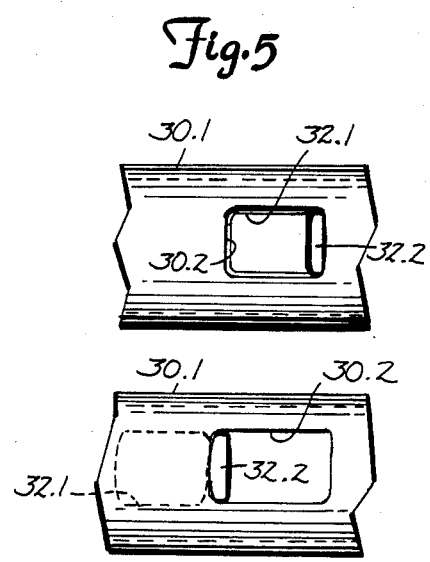
Fig.5
Fig.6

OSTOMY PROSTHESIS

TECHNICAL FIELD

This invention relates to the field of medical prosthetic devices and particularly to devices intended for use by ileostomy or colostomy patients.

BACKGROUND ART

Patients with surgical ostomy operations are routinely provided with externally worn ostomy bags. Such bags commonly have openings or mouths that are adhesively sealed to the skin of the patient about the ostomy stomas. Such bags must be periodically removed and emptied, of course. The adhesive seal between the mouth of the bag and the skin surrounding the stoma must be maintained airtight to prevent the escape of embarrassing odors. Often, the skin area surrounding the stoma to which the adhesive seal is applied becomes tender and painfully irritated, which irritations may be compounded by contact with bowel contents and may lead to serious infections.

One solution to this problem is to eliminate the need for an adhesively sealed ostomy bag. My U.S. Pat. No. 4,381,765, for example, discloses a medical prosthesis that includes a drainage tube, the inner end of which is secured to the stoma of a patient deep to the fascia and the outer end portion of which is releasably sealed. It is yet desirable, however, to provide ostomy patients with appropriate bags to collect bowel contents, but means are needed to avoid the heretofore necessary adhesive seal between the mouth of the bag and the skin of a patient.

DISCLOSURE OF THE INVENTION

The ostomy prosthesis of the invention includes a drainage tube having an inner end portion that is insertable within the ostomy stoma of a patient, and an outer end portion. Securing means are carried by the inner end portion of the drainage tube to secure the latter to the stoma deep to the fascia. Plate means are provided to flatly abut the skin of a patient adjacent the stoma, and means are provided to connect the outer end portion of the drainage tube to the plate means. The plate means is provided with an orifice positioned to define, with the outer end portion of the drainage tube, a passageway for the evacuation of bowel contents.

An ostomy bag is this embodiment is provided with a mouth, and sealing means are provided to seal the mouth of the bag to the plate means about the passageway to enable the bag to receive bowel contents issuing from the passageway. The prosthesis desirably includes manually operable closure means for releasably closing the passageway to prevent the escape of bowel contents. The bag in this embodiment has a flexible outer wall permitting manual manipulation of the manually operable closure means to open and close the passageway. In the manner thus described, the ostomy bag is sealingly secured to the ostomy opening, preventing the escape of bowel contents and odors, but yet is not adhered to the skin of the patient. Moreover, in the preferred embodiment, the flow of bowel contents into the bag can be regulated at will by the patient by manually opening and closing the passageway through the prosthesis.

BRIEF DESCRIPTION OF THE DRAWING

FIG. 2 is a broken-away, diagrammatic, cross-sectional view of another embodiment of an ostomy prosthesis of the invention;

FIG. 4 is a broken-away, cross-sectional, largely diagrammatic view of another embodiment of an ostomy prosthesis of the invention;

FIG. 5 is a cross-sectional view taken along line 5—5 of FIG. 4;

FIG. 6 is a view similar to that of FIG. 5 but showing another step in the use of the prosthesis; and FIG. 7 is a broken-away cross-sectional view of a preferred embodiment of a device of the invention.

BEST MODE FOR CARRYING OUT THE INVENTION

Figure 1:
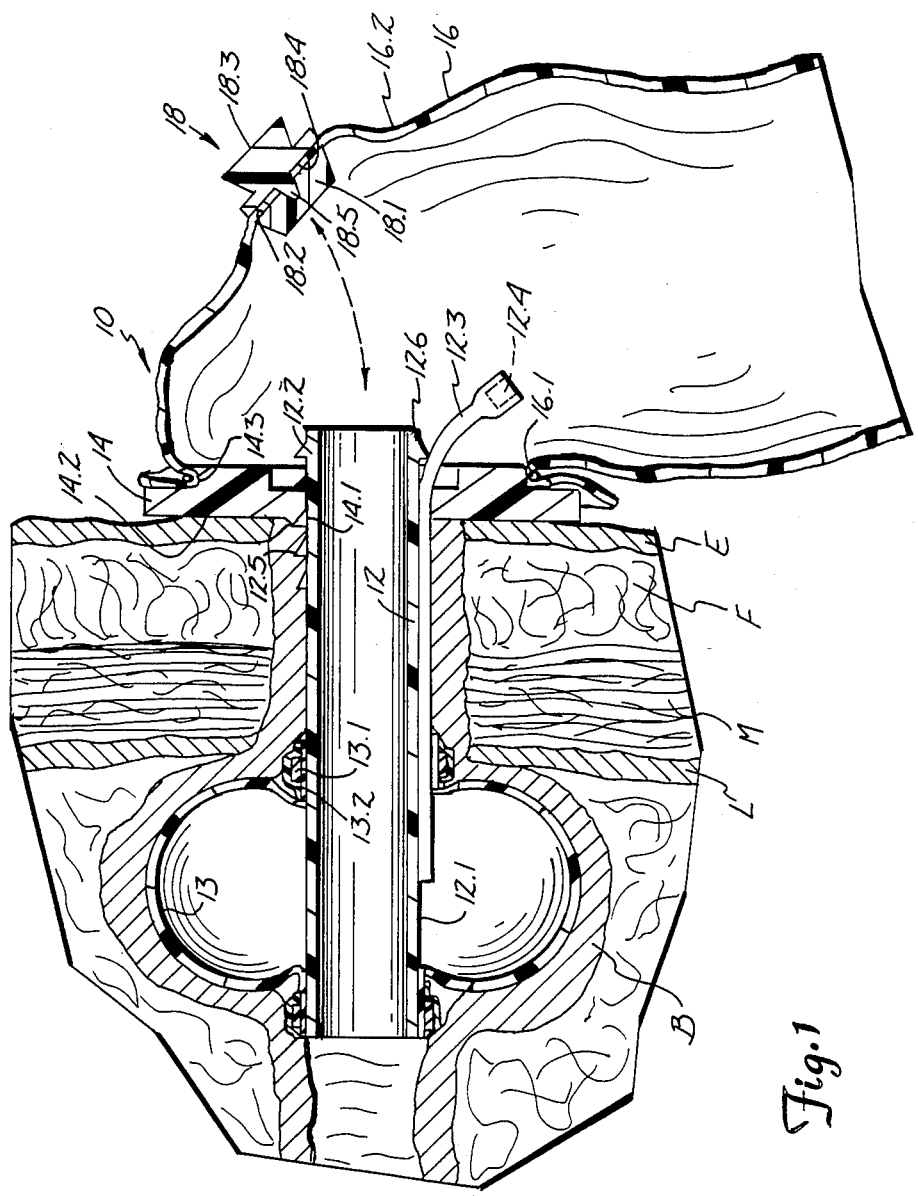
FIG. 1 is a broken-away, diagrammatic, cross-sectional view of an ostomy prosthesis of the invention showing the same secured within the stoma of a patient deep to the fascia.
Figure 3:
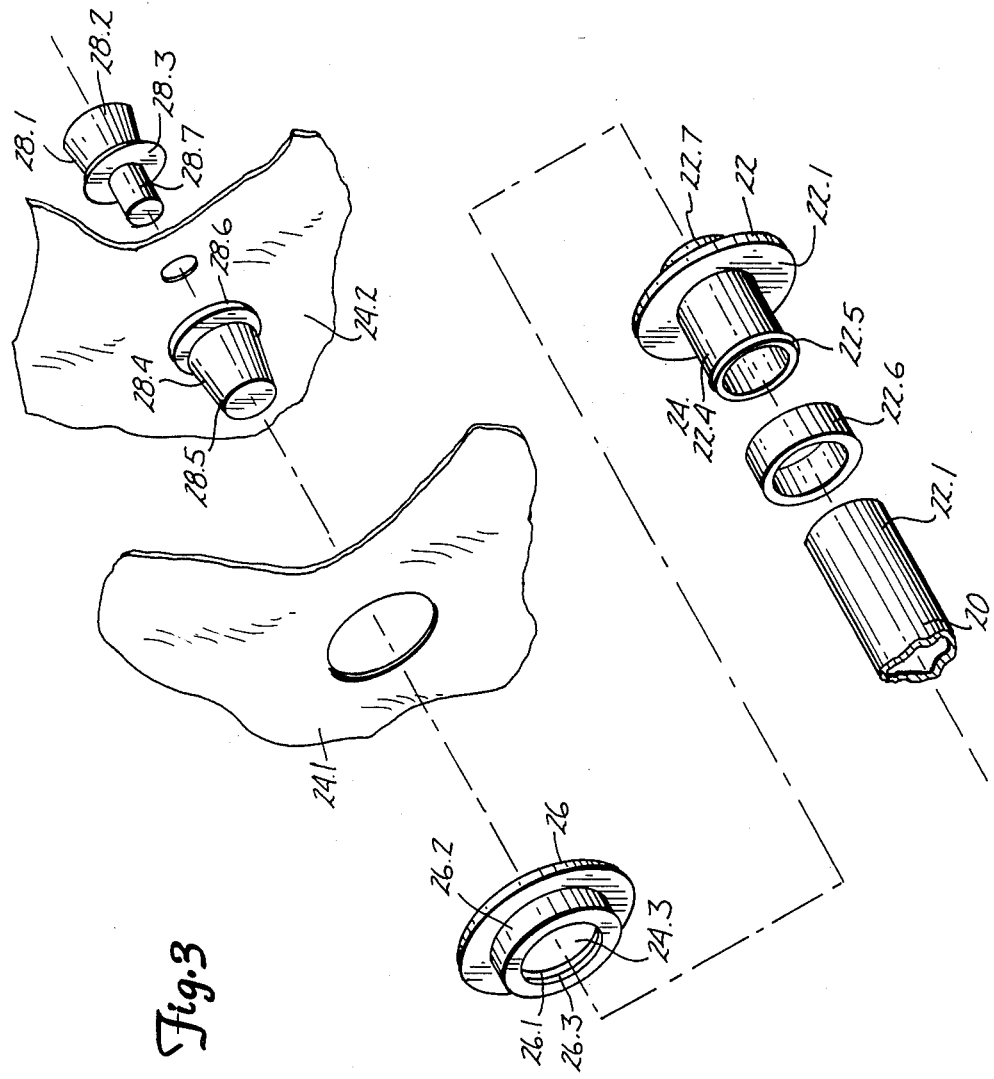
FIG. 3 is an exploded, diagrammatic view of a portion of the ostomy prosthesis of FIG. 2.

Referring first to FIG. 1, the ileostomy device of the invention is designated generally as (10), and includes a drainage tube (12) and an ostomy bag (16). The inner end portion (12.1) of the drainage tube is inserted and maintained within the stoma of a patient, the drainage tube extending forwardly and outwardly from the stoma.

In FIG. 1, "E" represents a patient's skin surrounding an ostomy stoma, "F" and "M", respectively, refer generally to layers of fat and muscle, and "L" refers to the abdominal fascia. The end portion of the bowel is depicted generally as "B", and, as shown in FIG. 1, the bowel extends forwardly and terminates at approximately the surface of the skin. In some instances, the bowel may protrude outwardly slightly of the skin surface.

The drainage tube (12) may be made of resilient silicone rubber or the like. Its inner end (12.1), as shown in FIG. 1, is received within the stoma of the patient deep to the fascia. A generally tubular length of thin-walled, resilient silicone rubber designated (13), overlays the inner portion (12.1) of the drainage tube. The ends of the thin-walled tubing length (13) are spaced from one another along the length of the drainage tube and are connected to the inner portion (12.1) of the drainage tube by means of relatively rigid annular bands (13.1) over which may be positioned wider silicone rubber supporting bands (13.2). As shown in FIG. 1, the tubing section (13) can be inflated by means of water or other fluid inserted under pressure through inflation tube (12.3), the section (13) thereby forming an annular, generally doughnut-shaped balloon structure which dilates the bowel "B" deep to the fascia and thus secures the drainage tube against being pulled forwardly out of the stoma. By releasing the pressure of fluid through the inflation tube (12.3), of course, the balloon structure may be deflated and the device may be readily removed from the stoma. Details of a construction of a balloon structure (13) are disclosed in my U.S. Pat. No. 4,381,765, the relevant teachings of which are incorporated herein by reference. The inflation tube (12.3) passes from the balloon structure (13) outwardly of the stoma, and may terminate forwardly in a generally cylindrical plug that is received within the tube, as shown at (12.4), the plug having a pierced hole therethrough within which may be inserted a blunted hypodermic needle to facilitate inflation and deflation of the balloon structure.

A plate (14), desirably generally circular, is provided with a central orifice (14.1) through which, in the embodiment of FIG. 1, the outer end (12.2) of the drainage tube passes. The outer drainage tube end (12.2) may have an outer, circumferential sawtooth structure as shown at (12.5) in FIG. 1 such that, as the plate (14) is pushed inwardly or rearwardly against the skin of a patient while concurrently pulling outwardly upon the drainage tube end (12.2), the plate orifice (14.1) will be captured behind one of the circumferential sawtooth ribs (12.5) to thus retain the tube in place. The inner surface (14.2) of the plate is shown in FIG. 1 as being in contact with the skin of a patient; it will be understood that gauze pads or other material may be employed between the plate (14) and the skin as desired so that the plate bears indirectly against the skin.

The plate (14) is provided with an annular shoulder (14.3) which is spaced away from the inner surface (14.2) of the plate. The circumferential outer surface of the shoulder (14.3) may be grooved, as shown in FIG. 1, and the mouth of an ileostomy bag (16) may be sealingly secured to the grooved shoulder (14.3) by means of a cord or elastic bands (16.1) or the like.

As shown in FIG. 1, the drainage tube (12) terminates forwardly in an annular rim (12.6) defining a plug seat. Plug means, shown generally at (18), is carried by the outer wall (16.2) of the bag and includes a plug (18.1) internally of the bag and sized to fit snugly within the rim (12.6) to thereby close the passageway defined by the drainage tube and the plate orifice. The tapered plug (18.1) is provided with a generally flat surface (18.2) facing the bag wall (16.2), and a separate, exterior handle portion (18.3) is provided similarly with a bag-facing surface (18.4). The handle portion may have a projection (18.5) that is received through a small aperture in the bag into a bore formed in the plug portion (18.1), all as shown in FIG. 1. The flat surfaces (18.2), (18.4) are carried on opposite surfaces of, and desirably are adhered to, the outer bag (16), thereby permitting the plug (18.1) to be manipulated through manual grasping of the handle portion (18.3).

As thus described, it will be understood that the passage leading through the drainage tube can be closed and opened at will by a patient through the simple expedient of inserting and removing the plug (18.1) from the plug seat defined by the drainage tube rim (12.6). It will be noted that the mouth of the ileostomy bag (16) is not adhered to the skin "E" of the patient, and it will also be noted that the bag (16) remains sealed to the plate (14) and hence to the ostomy opening regardless of whether the passageway is open or closed. The unplugged passageway is substantially free of obstructions tending to interfere with the free passage of bowel contents.

A modified embodiment of the invention is depicted in FIG. 2. In this Figure, the drainage tube is designated as (20) and the plate as (22). The inner end (not shown) of the drainage tube may be identical to that shown in FIG. 1.

The plate (22) desirably is generally circular, and includes a generally flat inner surface (22.1) and a central orifice (22.2), the outer portion of which is tapered as shown at (22.3) to provide a plug seat. The plate includes a coaxially extending, generally tubular portion (22.4) that terminates rearwardly in a radially outwardly extending, beveled shoulder (22.5). In this embodiment, the drainage tube is cut to the desired length for each patient so that when the outer end portion (20.1) of the drainage tube is slipped over the tubing section (22.4) of the plate and held in place with external band (22.6) and the inner surface (22.1) of the plate is held in snug abutment against the skin (including covered skin) of the patient, the inner end portion of the drainage tube (20) is secured within the stoma in the manner shown in FIG. 1. Again, gauze or other spacing material may be placed between the plate and the skin as desired. In a manner similar to that depicted in FIG. 1, the plate (22) is provided with a forwardly extending, annular, grooved shoulder (22.7).

An ileostomy bag is depicted in FIG. 2 generally as (24), and includes inner (toward the patient) and outer walls (24.1), (24.2). The mouth of the bag is shown generally as (24.3), and is formed in association with a disc (26) which is adhered or otherwise fixed to the surface of the inner wall (24.1), the disc having a central aperture (26.1) communicating with the interior of the bag. Extending from the disc coaxially with the aperture (26.1) is a short length of tubing (26.2) terminating in a radially inwardly protruding rim (26.3). The rim desirably is elastic, the orifice defined by the inner periphery of the rim being capable of elastically expanding so that the rim (24.5) may slip onto and be captured within the annular groove (22.7) of the plate (22) to thereby seal the bag to the plate.

Plug means is depicted in FIG. 2 generally as (28) and may be formed in two sections, of which one is an outer or handle section (28.1) having a graspable, forwardly protruding portion (28.2) and a flange (28.3) in contact with and desirably bonded to the outer surface of the outer bag wall (24.2). The inner plug portion, designated (28.4), includes an inwardly tapering plug portion (28.5) and a flange (28.6) lying against, and preferably bonded to, the inner surface of the bag wall (24.2) in alignment with the flange (28.3). If desired, a small connecting rod as shown at (28.7) may be carried by the plug portion (28.1) and may extend rearwardly through a small hole formed in the bag wall and into a receptive bore (28.8) formed in plug portion (28.4). The bag walls (24.1), (24.2) are flexible, in the usual manner, and as a result the plug handle (28.2) may be grasped and manipulated as desired.

With reference to the embodiment of FIG. 2, once the in-dwelling portion of the drainage tube and the plate (shown as the left-most element of FIG. 2) have been properly positioned with the plate lying snugly against the skin of the patient, a bag (24) may be rapidly and conveniently attached to the plate by simply stretching the elastic rim (26.3) over the annular shoulder (22.8) and into the groove (22.7). The plug (28) may then be moved into firm, sealing engagement within the plug seat (22.3) of the plate. At such time as it is desired to permit the flow of bowel contents through the drainage tube and into the bag, the patient merely grips the plug handle and pulls outwardly upon the plug (28) to open the passageway into the bag. The plug may then be simply replaced within the plug seat (22.3). Thus, the invention permits the bowel contents to be periodically emptied into an ostomy bag without removing the bag nor breaking the liquid and odor-proof seal between the bag and the stoma of the patient. This is particularly important when patients are first learning to wear a prosthesis of the type shown in FIG. 1 which, it will be understood, requires some bowel dilation.

Referring now to FIG. 4, a drainage tube is there depicted as (30), its forward end (30.1) being firmly attached to a skin-contacting plate (32) in the manner described with reference to FIG. 1. The rearward end of the tube (30) (not shown) may be secured within the bowel deep to the fascia in the manner depicted in FIG. 1. The mouth of the ostomy bag (34) is attached to an annular groove formed in the periphery of the plate (32) by means of an elastic cord or string (34.1).

In the embodiment of FIGS. 4-6, the outer end portion (30.1) of the drainage tube (30) is provided with a generally rectangular aperture (30.2) adjacent its end. A second tube (32), having an outer diameter approximately the same or very slightly smaller than the inner diameter of the tube (30), is inserted within the outer end of the tube (30) as shown in the drawing. The inner tube (32) similarly is provided with a generally rectangular aperture (32.1) adjacent its forward end and positioned so that as the inner tube (32) is moved axially within the tube (30), the two apertures may become aligned when the tube (32) is in its outermost position as shown in FIGS. 4 and 5. When the inner tube is moved to the left in FIG. 4, into the position shown in FIG. 6, the apertures (30.2), (32.1) are moved out of alignment, thereby sealing the drainage tube (30). A finger-like projection (32.2) extends radially outwardly from the inner tube (32) through the aperture (30.2) formed in the outer tube, the finger serving to restrain the amount of axial movement that is afforded the inner tube with respect to the outer tube.

It will be noted in the embodiment of FIG. 4 that the wall (34) of the ostomy bag is not attached to the closure means defined by the structure of the respective inner and outer tubes (32), (30). Rather, the end of the tube (32) includes a plate depicted as (32.3), the periphery of which can readily be grasped by the fingers through the flexible bag wall (34) in order to push or pull the inner tube to the desired closure or drainage position. FIG. 5 shows the alignment of apertures (30.2), (32.1) when the tube (32) is in the position shown in FIG. 4, bowel contents being permitted to drain into the bag (34). When the closure means is moved to the position shown in FIG. 6, on the other hand, the respective tube apertures are out of alignment and the passageway leading through the drainage tube is thus closed.

A presently preferred embodiment of the invention is illustrated in FIG. 7. In this embodiment, the drainage tube has a rearward end (not shown) that is provided with securing means such as that shown in FIG. 1 for securing the inner end of the drainage tube to the stoma of a patient deep to the fascia. A skin-contacting plate, designated (38) is attached to the forward end of the drainage tube. An annular groove (38.1) is formed in the plate coaxially with the central bore (38.2), the groove having a width approximately equal to the wall thickness of the end of the drainage tube (36). In this manner, the groove snugly receives and accommodates the everted end (38.3) of the drainage tube. The connection between the drainage tube and plate is formed by first passing the cut-to-length forward end of the drainage tube forwardly through the bore (38.2), then everting (that is, turning inside-out) the forward tube end (36.1) for a short distance, and then pulling the tube rearwardly again through the bore (38.2), the everted end (36.1) of the drainage tube being guided into the groove (38.1). The sharp-edged annular lip (38.3) formed between the bore (38.2) and the groove (38.1) of the plate thus seats between the opposing surfaces of the everted section of the tube and the adjacent tube. The connection thus formed has been found to be strong and creep-resistant. If desired, an adhesive may be used between the drainage tube end and lip (38.3) to more securely hold the tube in place. It will be noted that the forward rim (36.2) of the everted drainage tube end provides a smooth, circular opening readily receptive of a tapered plug when the drainage tube is to be closed.

The plate (38) may be provided with a suitable internal channel as shown at (38.4) through which the outer portion of an inflation tube (39) may pass, the inflation tube thus being continuously accessible to the wearer.

Adhered coaxially to the forward surface (38.5) of the plate (38) is an attachment flange (40.1) of an annular attachment plate (40), the latter having a short, tubular section (40.2) terminating forwardly in an outwardly turned rim (40.3). If desired, the tubular section (40.2) and rim (40.3) may be formed integrally on the forward face (38.5) of the plate (38).

An ostomy bag is shown generally as (42), and comprises inner and outer walls (42.1), (42.2) joined at their peripheries as by heat sealing to form an edge seal (42.3). An ostomy bag such as that shown at (42) is commonly provided with a circular opening (42.4) of sufficient diameter as to spacedly encircle the stoma of a patient; the openings may commonly range up to four or five centimeters in diameter. Adhered to the exterior surface (42.5) of the inner bag wall (42.1) about the opening (42.4) is an annular mounting flange (44.1) of a second annular attachment plate (44). This plate has a rearwardly (toward the patient) extending bore (44.2) within which is snugly received the tubular section (40.2) of the attachment plate (40). The annular plate (44) includes an annular shoulder (44.3) within which the rim (40.3) of the attachment plate (40) is received. The male and female annular attachment plates (40), (44) are sufficiently resilient as to enable them to be connected as shown in FIG. 7, the seal therebetween being substantially air-tight and hence odorproof.

Adhered to the inner surface (42.6) of the outer bag wall (42.2) is a plug (46) having a tapered, rearwardly extending nose (46.1) sized to be received snugly within the tubular rim (36.2) at the forward end of the drainage tube (36). The wall (42.2) is sufficiently flexible as to enable a user to grasp the outwardly extending shoulder (46.2) of the plug through the wall so that the plug nose can be maneuvered into and out of plugging engagement with the drainage tube rim (36.2).

The tubular section (40.2) typifies annular fastening means for fastening to the plate (38) a mating second annular fastening means (44) carried by the bag about its opening (42.4), and it will be noted that the annular fastening means (40.2) is carried forwardly (away from the patient) by the plate and is spaced forwardly from the rearward, skin-contacting surface (38.6) of the plate, thereby permitting the bag to be spaced outwardly slightly from the patient's skin. Of importance, of course, is the fact that no adhesive is required to hold the prosthesis of the invention to the skin of a patient; particularly, the ostomy bag is devoid of skin-contacting adhesive.

The drainage tubes described herein desirably are of silicone rubber or other biologically compatible material, and preferably are at least slightly flexible to permit them to be drawn through the ordinarily snugly fitting central orifice of the mounting plates. The latter, in turn, desirably are of a rigid material, desirably a plastic such as polycarbonate or the like. The plugs and the other closure structure adhered to or carried by the ostomy bag preferably are of silicone rubber. The ostomy bags are commonly made of flexible plastic material such as polyethylene or polypropylene. The bag materials desirably are substantially inert to the bowel contents, and the bag walls are sufficiently flexible as to enable the operation of the closure means as described above and also for the purpose of being able to conform comfortably to the body of the wearer.

While a preferred embodiment of the present invention has been described, it should be understood that various changes, adaptations and modifications may be made therein without departing from the spirit of the invention and the scope of the appended claims.

What is claimed is:

1. An ostomy prosthesis connectable to the stoma of a patient and including a drainage tube having an inner end portion insertable within the stoma of a patient and an outer end portion, securing means carried by the inner end portion for securing the latter to the stoma deep to the facia, and plate means for flatly abutting the skin of a patient adjacent the stoma, means connecting the outer end portion of the drainage tube to the plate means, the plate means including an orifice positioned to define, with the outer end portion of the drainage tube, a passageway for the evacuation of bowel contents, an ostomy bag having a mouth, and means sealing the mouth to the, plate means about the passageway to enable the bag to receive bowel contents therefrom.

2. The prosthesis of claim 1 including manually operable closure means for releasably closing said passageway to prevent the escape of bowel contents therefrom, the bag having a flexible outer wall enabling manual manipulation of the closure means to open and close the passageway.

3. The prosthesis of claim 2 wherein a portion of said closure means is mounted to the outer wall of the bag for manipulation by a patient.

4. The prosthesis of claim 2 in which the closure means comprises a push-pull valve and includes a graspable handle, and wherein the outer wall of the bag is sufficiently flexible as to enable the handle to be grasped through the flexible wall.

5. The prosthesis of claim 2 wherein the closure means comprises plug means carried by the outer wall of the bag and including a plug, and wherein said passageway terminates outwardly in a plug-receiving opening for receiving the plug to releasably close said passageway.

6. The prosthesis of claim 5 wherein said plug means comprises inner and outer disc members having confronting, generally flat surfaces affixed in mutually aligned orientation to oppose surfaces of the outer bag wall, the inner disc means carrying said plug.

7. The prosthesis of claim 1 wherein the plate includes an inner surface for facing the skin of a patient and wherein said sealing means comprises a first annular fastening means carried by the plate outwardly of the inner plate surface and a mating annular fastening means carried by the bag to sealingly engage the first fastening means.

8. The prosthesis of claim 7 wherein said mating annular fastening means includes means defining a resilient rim deformable to sealingly engage the first annular fastening means.

9. The prosthesis of claim 7 wherein the mating annular fastening means further includes a resilient flange attached to and carried by a wall of the ostomy bag, the flange having a central aperture communicating with the interior of the bag the flange including means defining a central resilient rim carried coaxially of the central aperture but spaced axially therefrom, said rim being adapted to sealingly engage the first annular fastening means carried by the plate means.

* * * * *